United States Patent [19] … [11] 4,219,657
Berger et al. … [45] Aug. 26, 1980

[54] DIBENZOTHIOPHENES

[75] Inventors: Leo Berger, Montclair; John T. Plati, Rutherford; Albert Ziering, Nutley, all of N.J.

[73] Assignee: Hoffmann-La Roche Inc., Nutley, N.J.

[21] Appl. No.: 861,746

[22] Filed: Dec. 19, 1977

Related U.S. Application Data

[63] Continuation of Ser. No. 669,940, Mar. 24, 1976, abandoned.

[51] Int. Cl.$^2$ .......................................... C07D 333/76
[52] U.S. Cl. .................................... 549/43; 424/275
[58] Field of Search ........................ 260/329.3; 549/43

[56] References Cited

U.S. PATENT DOCUMENTS 3,897,453   7/1975   Gante et al. ..................... 260/329.3

OTHER PUBLICATIONS

Campaigne et al., J. Heterocycl. Chem. 6(6), pp. 885–889, (1969); Index Chemicus 36: 134073 (1970).
Protiva et al., Czeck. Patent 129,655 (Nov. 15, 1968); Chem. Abst., vol. 72, col. P12727(s), (1970).
Buu-hoi, Ber. vol. 76B, pp. 1269–1274 (1943; Chem. Absts. vol. 39: 1408.
Southerwick et al., J. Am. Chem. Soc., vol. 83, pp. 1358–1368 (1961).
Gilman et al., J. Org. Chem., vol. 3, pp. 108–119 (1938); Chem. Abst. vol. 33, col. 580 (1939).

Primary Examiner—Norman Morgenstern
Assistant Examiner—L. Hendriksen
Attorney, Agent, or Firm—Jon S. Saxe; George M. Gould; Peter R. Shearer

[57] ABSTRACT

Dibenzothiophenes of the formula

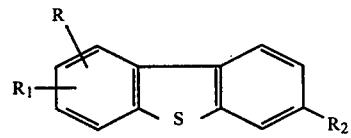

wherein R, $R_1$ and $R_2$ are as hereinafter described, prepared, inter alia, from the correspondingly substituted thiophenol and haloketocyclohexane are described. The dibenzothiophenes of the invention are useful antiinflammatory, analgesic and antirheumatic agents.

5 Claims, No Drawings

DIBENZOTHIOPHENES

This is a continuation of application Ser. No. 669,940, filed Mar. 24, 1976, now abandoned.

BRIEF SUMMARY OF THE INVENTION

The invention relates to compounds of the formula

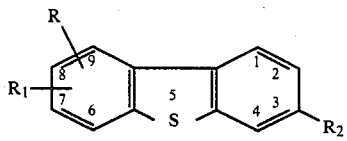

wherein R is hydrogen, halogen, hydroxy, cyano, lower alkyl, hydroxy-lower alkyl, lower alkoxy, acyl, benzyloxy, lower alkylthio, trifluoromethyl, nitro, amino, mono-lower alkylamino, di-lower alkylamino, sulfamoyl, di-lower alkylsulfamoyl or difluoromethylsulfonyl; $R_1$ is halogen, cyano, lower alkyl, hydroxy-lower alkyl, lower alkoxy, acyl, acylamido, benzyloxy, lower alkylthio, trifluoromethyl, hydroxy, nitro, amino, mono-lower alkylamino, di-lower alkylamino, sulfamoyl, di-lower alkylsulfamoyl or difluoromethylsulfonyl, or R taken together with an adjacent $R_1$ is also lower alkylenedioxy; $R_2$ is

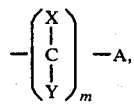

wherein A is hydroxy, lower alkoxy, amino-lower alkoxy, mono-lower alkylamino-lower alkoxy or di-loweralkylamino-lower alkoxy, X and Y, independently, are hydrogen or lower alkyl, and m is 1 to 7, or $R_2$ is

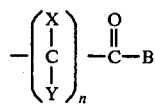

wherein B is hydroxy, carboxy, lower alkoxy, amino, hydroxyamino, mono-lower alkylamino, di-lower alkylamino, amino-lower alkoxy, mono-lower alkylamino-lower alkoxy or di-lower alkylamino-lower alkoxy, Y and X, independently, are hydrogen or lower alkyl; and n is 1 to 7; when X and Y are different, their enantiomers; when B is hydroxy or carboxy, salts thereof with pharmaceutically acceptable bases; and when R or $R_1$ is amino, mono-lower alkylamino or di-lower alkylamino, and/or when B or A is amino-lower alkoxy, mono-lower alkylamino-lower alkoxy or di-lower alkylamino-lower alkoxy, addition salts thereof with pharmaceutically acceptable acids. The dibenzothiophenes of formula I are useful as antiinflammatory, analgesic and antirheumatic agents.

DETAILED DESCRIPTION OF THE INVENTION

As used herein, the term "lower alkyl" denotes a straight or branched chain hydrocarbon group containing 1-7 carbon atoms, for example, methyl, ethyl, propyl, isopropyl, butyl, isobutyl, tertiary butyl, neopentyl, pentyl, heptyl and the like. The term "lower alkoxy" denotes an alkyl ether group in which the alkyl group is as described above, for example, methoxy, ethoxy, propoxy, isopropoxy, butoxy, pentoxy and the like. The term "lower alkylthio" denotes an alkyl thioether group in which the alkyl group is as described above, for example, methylthio, ethylthio, propylthio, isopropylthio, butylthio, pentylthio and the like. The term "halogen" denotes all the halogens, that is, bromine, chlorine, fluorine and iodine; bromine and chlorine are preferred. The term "acyl" denotes an "alkanoyl" group derived from an aliphatic carboxylic acid of 1 to 7 carbon atoms, for example, formyl, acetyl, propionyl, and the like, and an "aroyl" group derived from an aromatic carboxylic acid, such as benzoyl and the like. The term "lower alkylene" denotes a straight or branched chain alkylene of 1-7 carbon atoms, for example, methylene, ethylene, propylene, butylene, methylmethylene and the like. The term "lower alkylenedioxy" preferably denotes methylenedioxy and the like.

Exemplary of mono-lower alkylamino are methylamino, ethylamino and the like. Exemplary of di-lower alkylamino are dimethylamino, diethylamino and the like. Exemplary of amino-lower alkoxy are aminomethoxy, aminoethoxy and the like. Exemplary of mono-lower alkylamino-lower alkoxy are methylamino-methoxy ethylaminoethoxy and the like. Exemplary of di-lower alkylamino-lower alkoxy are dimethylaminomethoxy, diethylaminoethoxy and the like. Exemplary of di-lower alkylsulfamoyl are dimethylsulfamoyl, diethylsulfamoyl and the like.

The invention relates to compounds of the formula

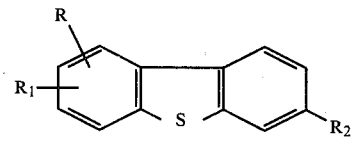

wherein R is hydrogen, halogen, hydroxy, cyano, lower alkyl, hydroxy-lower alkyl, lower alkoxy, acyl, benzyloxy, lower alkylthio, trifluoromethyl, nitro, amino, mono-lower alkylamino, di-lower alkylamino, sulfamoyl, di-lower alkylsulfamoyl or difluoromethylsulfonyl; $R_1$ is halogen, cyano, lower alkyl, hydroxy-lower alkyl, lower alkoxy, acyl, acylamido, benzyloxy, lower alkylthio, trifluoromethyl, hydroxy, nitro, amino, mono-lower alkylamino, di-lower alkylamino, sulfamoyl, di-lower alkylsulfamoyl or difluoromethylsulfonyl, or R taken together with an adjacent $R_1$ is also lower alkylenedioxy; $R_2$ is

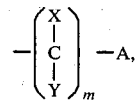

wherein A is hydroxy, lower alkoxy, amino-lower alkoxy, mono-lower alkylamino-lower alkoxy or di-lower alkylamino-lower alkoxy, Y and X, independently, are hydrogen or lower alkyl, and m is 1 to 7, or $R_2$ is

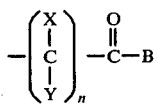

wherein B is hydroxy, carboxy, lower alkoxy, amino, hydroxyamino, mono-lower alkylamino, di-lower alkylamino, amino-lower alkoxy, mono-lower alkylamino-lower alkoxy or di-lower alkylamino-lower alkoxy; Y and X, independently, are hydrogen or lower alkyl; and n is 1 to 7; and when X and Y are different, their enantiomers; when B is hydroxy or carboxy, salts thereof with pharmaceutically acceptable bases; and when R or $R_1$ is amino, mono-lower alkylamino or di-lower alkylamino, and/or when B or A is amino-lower alkoxy, mono-lower alkylamino-lower alkoxy or di-lower alkylamino-lower alkoxy, addition salts thereof with pharmaceutically acceptable acids.

Preferred dibenzothiophenes of the invention are those characterized by the formulas

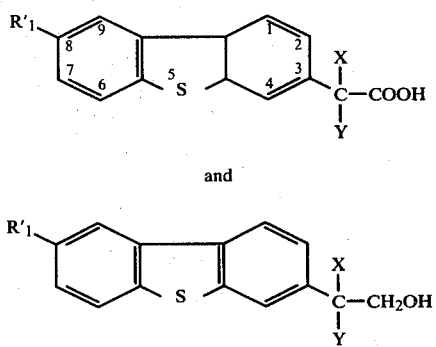

wherein $R'_1$ is halogen, lower alkyl or lower alkoxy, preferably $R'_1$ is halogen or lower alkyl, and most preferably $R'_1$ is halogen, and X and Y are as previously described, their enantiomers when X and Y are different, and salts of the compounds of formula I' with pharmaceutically acceptable bases. Preferably, in formula I, m is 2 and n is 1.

Preferred compounds of formula I are:
racemic 8-chloro-α-methyl-dibenzothiophene-3-acetic acid;
(+) 8-chloro-α-methyl-dibenzothiophene-3-acetic acid;
(−) 8-chloro-α-methyl-dibenzothiophene-3-acetic acid;
racemic 2-(8-chloro-3-dibenzothienyl)propanol;
2-(8-chloro-3-dibenzothienyl)ethanol;
8-chloro-dibenzothiophene-3-acetic acid;
8-chloro-dibenzothiophene-3-acetamide.

Examplary of compounds of this invention corresponding to formula I are:
8-chloro-dibenzothiophene-3-acetic acid;
8-chloro-dibenzothiophene-3-acetic acid ethyl ester;
8-methoxy-dibenzothiophene-3-acetic acid;
8-nitro-dibenzothiophene-3-acetic acid;
7-methoxy-dibenzothiophene-3-acetic acid;
7-chloro-dibenzothiophene-3-acetic acid;
8-methyl-dibenzothiophene-3-acetic acid;
6-chloro-dibenzothiophene-3-acetic acid;
8,9-dichloro-dibenzothiophene-3-acetic acid;
α-methyl-dibenzothiophene-3-acetic acid;
7-methyl-dibenzothiophene-3-acetic acid;
7,8-dichloro-dibenzothiophene-3-acetic acid;
8-chloro-9-methyl-dibenzothiophene-3-acetic acid;
8-difluoromethylsulfonyl-dibenzothiophene-3-acetic acid;
racemic 2-(8-chloro-3-dibenzothienyl)propanol methyl ether;
8-chloro-7-methyl-dibenzothiophene-3-acetic acid;
8-sulfamoyl-dibenzothiophene-3-acetic acid;
8-benzoyl-dibenzothiophene-3-acetic acid;
8-fluoro-dibenzothiophene-3-acetic acid;
8-trifluoromethyl-dibenzothiophene-3-acetic acid;
6,7-dichloro-dibenzothiophene-3-acetic acid;
9-chloro-8-sulfamoyl-dibenzothiophene-3-acetic acid;
8-methylthio-dibenzothiophene-3-acetic acid;
8-ethyl-dibenzothiophene-3-acetic acid;
8-chloro-dibenzothiophene-3-acetic acid dimethylaminoethyl ester;
8-methyl-dibenzothiophene-3-acetic acid ethyl ester;
8-dimethylsulfamoyl-dibenzothiophene-3-acetic acid;
8-iodo-dibenzothiophene-3-acetic acid;
8-chloro-N,N-dimethyl-dibenzothiophene-3-acetamide;
8-cyano-dibenzothiophene-3-acetic acid;
8-acetyl-dibenzothiophene-3-acetic acid;
8-chloro-dibenzothiophene-3-acetic acid dimethylaminoethyl ester hydrochloride;
8-benzyloxy-dibenzothiophene-3-acetic acid;
7,8-methylenedioxy-dibenzothiophene-3-acetic acid;
8-hydroxy-dibenzothiophene-3-acetic acid;
7-chloro-dibenzothiophene-3-acetic acid ethyl ester;
9-chloro-dibenzothiophene-3-acetic acid ethyl ester;
8-bromo-dibenzothiophene-3-acetic acid ethyl ester;
8-acetamido-dibenzothiophene-3-acetic acid ethyl ester;
8-chloro-dibenzothiophene-3-propionic acid ethyl ester;
8-chloro-α,α-dimethyl-dibenzothiophene-3-acetic acid ethyl ester;
8-chloro-α-methyl-dibenzothiophene-3-acetic acid dimethylaminoethyl ester;
8-chloro-α-methyl-dibenzothiophene-3-acetamide;
8-trifluoromethyl-dibenzothiophene-3-acetic acid ethyl ester;
6,7-dichloro-dibenzothiophene-3-acetic acid ethyl ester;
8,9-dichloro-dibenzothiophene-3-acetic acid ethyl ester;
8-methylthio-dibenzothiophene-3-acetic acid ethyl ester;
8-fluoro-dibenzothiophene-3-acetic acid ethyl ester;
α-methyl-dibenzothiophene-3-acetic acid ethyl ester;
8-N,N-dimethylsulfamoyl-dibenzothiophene-3-acetic acid ethyl ester;
7,8-dichloro-dibenzothiophene-3-acetic acid ethyl ester;
8-nitro-dibenzothiophene-3-acetic acid ethyl ester;
7-dimethylaminodibenzothiophene-3-acetic acid ethyl ester; and the like.

The compounds of formula I can be prepared by alkylating a compound of the formula

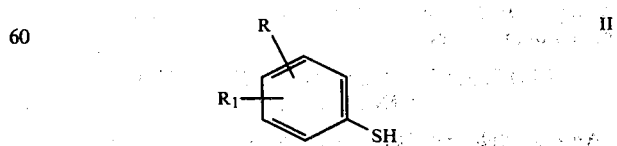

wherein R and $R_1$ are as previously described, with the corresponding haloketocycloalkane compound of the formula

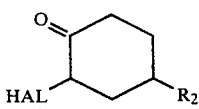

wherein HAL and R₂ are as previously described, to yield a compound of the formula

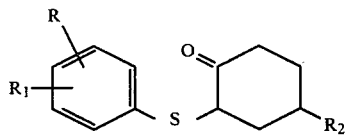

wherein R, R₁ and R₂ are as previously described.

The reaction is conveniently carried out in a nonpolar solvent, for example, a hydrocarbon, such as benzene, toluene and the like, or a polar solvent, such as dimethylsulfoxide, dimethylformamide, hexamethylphosphoric triamide, an alkanol such as ethanol, and the like. The reaction temperature is not critical. Preferably, the reaction is carried out at a temperature in the range of from about room temperature to about the reflux temperature of the reaction mixture. The molar ratio of the reactants is not critical. Preferably, they are reacted at a 1:1 molar ratio.

A compound of formula IV is converted to a compound of the formula

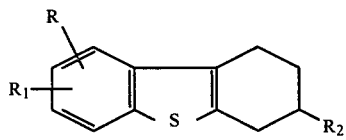

wherein R, R₁ and R₂ are as previously described, by thermal cyclization or by utilizing a cyclizing agent, such as polyphosphoric acid, and the like. Preferably, the reaction is carried out at a temperature in the range of from about −20° to about 120°. The reaction can be conveniently carried out with or without a solvent. Exemplary of convenient solvents are acetic acid and the like.

An ester of formula I can be converted to the corresponding acid, i.e., the compounds of formula I wherein B is hydroxy, by saponification according to known procedures, for example, by reaction with an alkali metal hydroxide such as sodium hydroxide, potassium hydroxide and the like, and subsequent treatment with a mineral acid, for example, a hydrohalic acid such as hydrochloric acid or the like. Additionally, an ester of formula I can be converted to the corresponding acid by treatment with a mineral acid, for example, a hydrohalic acid such as hydrochloric acid or the like, in the presence of an organic solvent such as acetic acid, preferably at the reflux temperature of the reaction mixture.

The separation of the desired compound of formula I and its corresponding acid from the reaction mixture can be effected utilizing known techniques such as, for example, filtration, crystallization, distillation and the like.

Furthermore, a salt of an acid of formula I, i.e., a salt of compounds of formula I wherein B is hydroxy, can be converted to a compound of formula I wherein B is amino-lower alkyl, mono-lower alkylamino-lower alkyl or di-lower alkylamino-lower alkyl by known procedures. For example, a salt of an acid of formula I is reacted with an amino-lower alkyl halide, mono-lower alkylamino-lower alkyl halide or di-lower alkylamino-lower alkyl halide, exemplary of which are aminoethyl chloride, methylamino-ethyl bromide, diethylaminomethyl chloride and the like, to yield the desired end product. The temperature at which the reaction is effected is not critical; conveniently, the reaction is carried out at a temperature in the range of from about room temperature to about the reflux temperature of the reaction mixture. Conveniently, the reaction can be carried out in a polar solvent, such as dimethylformamide, dimethylsulfoxide or the like. The molar ratio of reactants is not critical. Preferably, the reactants are utilized in a 1:1 molar ratio.

The starting materials of formula II are known compounds or can be prepared in an analogous manner to known compounds. Exemplary of such compounds are:
4-chlorothiophenol;
5-chlorothiophenol; and
4-nitrothiophenol.

The starting materials of formula III can be prepared by halogenating a compound of the formula

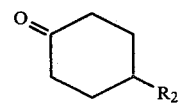

wherein R₂ is as previously described; to yield a compound of the formula

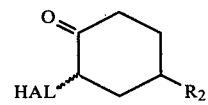

wherein HAL and R₂ are as previously described.

The compounds of formula VI are known compounds or can be prepared in an analogous manner to known compounds.

The halogenation is effected utilizing known procedures, for example, utilizing a halogen such as bromine in ether, at a temperature of −10° C. Exemplary of such compounds are:
3-bromo-4-ketocyclohexaneacetic acid;
3-bromo-4-ketocyclohexaneacetic acid ethyl ester; and the like.

Exemplary of the intermediates of formula IV are:
3-(4-chloro-phenylthio)-4-oxocyclohexaneacetic acid and ethyl ester thereof;
3-(4-bromo-phenylthio)-4-oxocyclohexaneacetic acid and methyl ester thereof; and the like.

The 1,2,3,4-tetrahydrodibenzothiophenes of formula V are then aromatized to the corresponding compound of formula I.

A compound of formula V is converted to a compound of formula I utilizing a dehydrogenating agent, for example, p-chloranil, o-chloranil, 2,3-dichloro-5,6-dicyanobenzoquinone (DDQ), sulfur, palladium on carbon, lead oxide, and the like, in the presence of a solvent, for example, xylene, benzene, toluene, quinoline, dimethylsulfoxide (DMSO), dioxane, dimethylformamide (DMF). The aromatization is carried out at a temperature in the range of from about room temperature to about the reflux temperature of the reaction mixture;

preferably, it is carried out at the reflux temperature of the reaction mixture. The compound of formula I can be separated from the reaction mixture by known procedures, included among which are, for example, filtration, crystallization, distillation, and the like. 7-Nitrodibenzothiophene-3-carboxylic acid ethyl ester 5-oxide is made by nitration of dibenzothiophene-3-carboxylic acid ethyl ester 5-oxide which in turn is made by oxidation of dibenzothiophene-3-carboxylic acid ethyl ester with chlorine.

An acid of formula I, wherein B is hydroxy, can be converted to the corresponding ester by known procedures. For instance, (a) an acid of formula I can be reacted with an alkanol such as methanol, ethanol, propanol or the like, in the presence of an acid catalyst, at a temperature in the range of from about room temperature to the reflux temperature of the reaction mixture, or (b) an alkali metal salt of an acid of formula I, such as the sodium salt, can be reacted with a substituted or unsubstituted alkyl halide utilizing known reaction conditions, for example, in an inert solvent such as benzene, toluene, dimethylformamide or the like, at a temperature in the range of from about room temperature to the reflux temperature of the reaction mixture.

A compound of formula I, wherein R or $R_1$ is amino, can be converted to the corresponding compound wherein R or $R_1$ is dialkylamino, utilizing known procedures, for example, utilizing hydrogen at a pressure of from about 1 atmosphere to about several atmospheres and a catalyst such as Raney nickel, together with an alkyl aldehyde such as formaldehyde, at a temperature in the range of from about room temperature to about 100°, in a solvent, for example, an alkanol such as methanol, ethanol or the like. The alkylation can also be carried out by treating the amine, for example, with trimethylphosphate under known conditions.

A compound of formula I, wherein R, $R_1$ or A is alkoxy, can be converted to the corresponding compound, wherein R, $R_1$ or A is hydroxy, by known procedures. For example, a compound of formula I bearing an alkoxy group can be treated with a mineral acid, for example, a hydrohalic acid such as hydrobromic acid, or the like, in a solvent, for example, alkanols such as ethanol, propanol, or the like, at a temperature in the range of from about room temperature to about the reflux temperature of the reaction mixture. The conversion can also be effected utilizing a Lewis acid, such as aluminum tribromide, aluminum trichloride, boron bromide, tin tetrachloride or the like, in a solvent such as benzene, toluene, dimethylformamide or the like.

An alcohol of formula I, i.e., an alcohol prepared from the corresponding ketone of formula III, wherein A is hydroxy, can be converted to the corresponding compound of formula I wherein A is lower alkoxy, amino-lower alkoxy, mono-lower alkylamino-lower alkoxy or di-lower alkylamino-lower alkoxy by known procedures. For example, an alcohol of formula I, wherein A is hydroxy, is treated with an alkali metal such as sodium. The resulting compound is then treated with a halide (X) of the formula RX, wherein R is lower alkyl, amino-lower alkyl, mono-lower alkylamino-lower alkyl or di-lower alkylamino-lower alkyl, utilizing known reaction conditions.

A compound of formula I, wherein B is lower alkoxy, can be de-esterified to the corresponding compound of formula I wherein B is hydroxy, with an alkali hydroxide, such as sodium hydroxide, potassium hydroxide or the like, in the presence of a solvent, for example, an alkanol such as methanol, ethanol or the like. The de-esterification can be carried out at a temperature in the range of from about room temperature to about the reflux temperature of the reaction mixture, preferably, it is carried out at the reflux temperature of the reaction mixture. The compound of formula I can be separated from the reaction mixture by known procedures. The de-esterification can also be carried out utilizing an acid such as hydrochloric acid under known conditions.

An ester of formula I can be converted to the corresponding alcohol, e.g., wherein A is hydroxy, by known procedures. For example, an ester of formula I can be treated with a reagent such as lithium aluminum hydride, at a temperature in the range of from about room temperature to the reflux temperature of the reaction mixture. Thereafter, the corresponding alcohol which is formed can be separated by known procedures.

A compound of formula I, wherein n is 1, X and Y are hydrogen and B is lower alkoxy, e.g., dibenzothiophene-3-acetic acid ethyl ester, 8-methyldibenzothiophene-3-acetic acid ethyl ester and 7-dimethylaminodibenzothiophene-3-acetic acid ethyl ester can be synthesized from the corresponding carboxylic acids, for example, dibenzothiophene-3-carboxylic acid, 8-methyldibenzothiophene-3-carboxylic acid and 7-dimethylaminodibenzothiophene-3-carboxylic acid via the Arndt-Eistert reaction which involves conversion of the carboxylic acids to the acid chlorides followed by reaction with diazomethane to yield the diazoketones. Rearrangement in alcohol solution in the presence of silver ion yielded the corresponding acetic acid ethyl esters.

A compound of formula I, wherein $R_1$ is acylamido, can be converted to the corresponding compound of formula I, wherein $R_1$ is amino, by treatment with an inorganic acid, for example, a hydrohalic acid such as hydrochloric acid or the like, utilizing known reaction conditions.

Alkylation of 8-chlorodibenzothiophene-3-acetic acid ethyl ester in the alpha-position can be carried out by dissolving the ester in liquid ammonia containing sodium amide and then adding methyl iodide or butyl bromide to produce either 8-chloro-alpha-methyldibenzothiophene-3-acetic acid ethyl ester or 8-chloro-alpha-butyldibenzothiophene-3-acetic acid ethyl ester. Realkylating 8-chloro-alpha-methyldibenzothiophene-3-acetic acid ethyl ester with methyl iodide as above yields the 8-chloro-alpha,alpha-dimethyldibenzothiophene-3-acetic acid ethyl ester. Hydrolysis of the ester yields the corresponding acids.

The acids of formula I, i.e., the compounds of formula I, wherein B is hydroxy, and salts of such acids with bases, can be converted to a compound of formula I wherein B is amino-lower alkoxy, mono-lower alkylamino-lower alkoxy or di-lower alkylamino-lower alkoxy by known procedures. For example, a salt of an acid of formula I is reacted with an amino-lower alkyl halide, mono-lower alkylamino-lower alkyl halide or di-lower alkylamino-lower alkyl halide, exemplary of which are aminoethyl chloride, methylamino-ethyl bromide, diethylaminomethyl chloride and the like, to yield the desired end product. The temperature at which the reaction is effected is not critical; conveniently, the reaction is carried out at a temperature in the range of from about room temperature and about the reflux temperature of the reaction mixture. Conveniently, the reaction can be carried out in a polar solvent, such as dimethylformamide, dimethylsulfoxide or the like. The molar ratio of reactants is not critical. Preferably, the reactants are utilized in a 1:1 molar ratio.

The compounds of formula I when R or $R_1$ is amino, mono-lower alkylamino, di-lower alkylamino, and/or when B or A is amino-lower alkoxy, mono-lower alkylamino-lower alkoxy or di-lower alkylamino-lower alkoxy, form addition salts with pharmaceutically acceptable organic or inorganic acids such as hydrohalides, e.g., hydrochloride, hydrobromide, hydroiodide, other mineral acid salts such as sulfate, nitrate, phosphate and the like, alkyl- and mono-arylsulfonates such as ethanesulfonate, toluenesulfonate, benzenesulfonate, or the like, other organic acid salts such as acetate, tartrate, maleate, citrate, benzoate, salicylate, ascorbate and the like.

The compounds of formula I, when B is hydroxy or carboxy, form salts with pharmaceutically acceptable bases. Exemplary of such bases are alkali metal hydroxides, such as sodium hydroxide, potassium hydroxide, and the like; alkaline earth hydroxides, such as calcium hydroxide, barium hydroxide and the like; sodium alkoxides, such as sodium ethanolate, potassium ethanolate and the like; organic bases such as piperidine, diethanolamine, N-methylglucamine, and the like. Also included are the aluminum salts of the compounds of formula I, as above.

The compounds of formula I, including the salts of those compounds of formula I which form salts with pharmaceutically acceptable bases and acids, possess anti-inflammatory, analgesic and anti-rheumatic activity, and are therefore useful as anti-inflammatory, analgesic and anti-rheumatic agents. The compounds of formula I also exhibit a significantly low incidence of ulcerogenic activity, which renders them highly desirable as anti-inflammatory, analgesic and anti-rheumatic agents. Their pharmacologically useful activities are demonstrated in warm-blooded animals using standard procedures.

For example, the anti-inflammatory activity is demonstrated in Albino rats of Hart Strain, weighing 125–155 gms. The test animals are given 10 mls. of vehicle[1], which contains the test compound per kg. of body weight. The animals are treated daily for 5 consecutive days. Three hours after the first treatment, 0.05 ml. of an 0.5% suspension of heat killed dessiccated *Mycobacterium butyricum* in U.S.P. olive oil, which has been steam sterilized for 30 minutes, is injected into the right hind foot of each rat. The paw volume is measured immediately after the injection of the adjuvant and again 96 hours later. The difference is recorded as volume of edema. The paw volume is measured by immersion of the paw into a column of mercury to an ink mark exactly at the level of the lateral malleolus. Percent inhibition is calculated by dividing the average control edema minus the average treatment edema by the average control edema times 100. The percent inhibition is plotted against dose on semi-logarithmic probability paper and the dose required to produce a 30% reduction in edema is estimated therefrom and is expressed as $ED_{30}$.

[1] Hilgar, A. G. and Hummel, D. J.: Endocrine Bioassay Data. No. 1, p. 15, August 1964 (Cancer Chemotherapy National Service Center, N.I.H.)

When 8-chloro-dibenzothiophene-3-acetic acid, which has demonstrated an $LD_{50}$ of, for example, 775 mg. p.o. in mice, is utilized as the test substance at a dosage of 0.03 gm. p.o., an anti-inflammatory activity is observed ($ED_{30} = 1.8$ mg/kg/day).

The analgesic activity of the compounds of the invention is demonstrated, for example, employing the method which is a modification of that described by Eddy (1950), Wolfe and MacDonald (1944) and Eddy and Leimbach (1952). The method determines the reaction time of mice dropped onto a hot plate maintained at $55 \pm 0.5°$ C. Six groups of male mice (5 mice/group) weighing between 20–30 grams are utilized. The initial reaction time of these mice is determined once, and the reaction time of each group is then averaged. The mice are then administered the vehicle and/or the compound to be tested by the oral, intraperitoneal or subcutaneous route. The average reaction time of each group is determined again at 30, 60 and 90 minutes after compound administration and is compared to controls. Reaction time is recorded as percent changes from control. All groups are averaged before and after treatment. A combined reaction time average (recorded as percent change of reaction time threshhold from controls) for all three periods is plotted against does on graph paper, and a curve is drawn. The $ED_{50}$ is read from this curve.

When 8-chloro-dibenzothiophene-3-acetic acid, which has demonstrated an $LD_{50}$ of, for example, 775 mg. p.o. in mice, is utilized as the test substance, analgesic activity is observed at an $ED_{50}$ of 120 mg/kg after oral administration.

The compounds of formula I, their enantiomers and salts thereof as herein described, have effects qualitatively similar to those of phenylbutazone and indomethacin, known for their therapeutic uses and properties. Thus, the end products of this invention demonstrate a pattern of activity associated with anti-inflammatory agents of known efficacy and safety.

The compounds of formula I, their enantiomers and salts thereof as herein described, can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkylene-glycols, and the like. The pharmaceutical preparations can be employed in a solid form, for example, as tablets, troches, suppositories, capsules, or in liquid form, for example, as solutions, suspensions, or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

Since the compounds of the invention when X and Y in formula I are different possess an asymmetric carbon atom, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture with an optically active resolving agent, for example, an optically active base, such as d-α-methylbenzylamine, which can be reacted with the carboxyl group. The formed diastereomers are separated by selective crystallization and converted to the corresponding optical isomer. Thus, the invention covers the racemates of the compounds of formula I as well as their optically active isomers.

The following Examples further illustrate the invention. All temperatures are in degrees Centigrade, unless otherwise stated.

EXAMPLE 1

Preparation of 8-chloro-α-methyldibenzothiophene-3-acetic acid

To a 500 ml. three-necked flask containing 100 ml. of liquid ammonia and 0.009 mol of sodium amide (prepared from 0.2 g. sodium) was added dropwise a solution of 2.6 g. of 8-chlorodibenzothiophene-3-acetic acid ethyl ester in 20 ml. of ether and 10 ml. of tetrahydrofuran. The solution was stirred for 1 hour and then a solution of 1.3 g. of methyl iodide in 20 ml. of ether was added dropwise. After the solution was stirred for 1 hour, 0.5 g. of ammonium chloride was added and the ammonia allowed to evaporate. Then the residue was acidified with dilute hydrochloric acid and the oil extracted with ether. The ether was removed and the residue slowly solidified. The solid was crystallized from pentane and yielded 1.5 g. of 8-chloro-α-methyldibenzothiophene-3-acetic acid ethyl ester, m.p. 73°–75°.

1.3 G. of 8-chloro-α-methyldibenzothiophene-3-acetic acid ethyl ester was added to 100 ml. of absolute ethanol containing 0.6 g. of potassium hydroxide. The solution was refluxed for 3 hours. Then the solvent was removed in vacuo and the residue dissolved in 30 ml. of water. The solution was acidified with dilute hydrochloric acid and the oil extracted with ether. The ether was removed and the residue, crystallized from ethyl acetate, yielded 0.9 g. of 8-chloro-α-methyldibenzothiophene-3-acetic acid, m.p. 190°–192°.

EXAMPLE 2

Preparation of 8-chloro-α,α-dimethyldibenzothiophene-3-acetic acid

To a 500 ml. three-necked flask containing 400 ml. of liquid ammonia and 0.017 mol of sodium amide (prepared from 0.39 g. of sodium) was added dropwise a solution of 5.1 g. of 8-chloro-α-methyldibenzothiophene-3-acetic acid ethyl ester in 40 ml. of tetrahydrofuran. The solution was stirred for 1 hour and then a solution of 2.3 g. of methyl iodide in 50 ml. of ether was added dropwise. After the addition, the solution was stirred for 3 hours. Then 1.1 g. of ammonium chloride was added and the ammonia allowed to evaporate. The residue was acidified with dilute hydrochloric acid and the oil extracted with ether. The ether was removed and the residue, crystallized from pentane, yielded 1.8 g. of 8-chloro-α,α-dimethyldibenzothiophene-3-acetic acid ethyl ester, m.p. 57°–61°.

1.8 G. of 8-chloro-α,α-dimethyldibenzothiophene-3-acetic acid ethyl ester was added to a solution of 0.4 g. of potassium hydroxide in 100 ml. of ethanol. After the solution had refluxed for 3 hours, the solvent was removed in vacuo. The residue was dissolved in 75 ml. of water and the solution acidified with dilute hydrochloric acid. The crude acid was extracted with ethyl acetate. The solvent was removed in vacuo and the residue, crystallized from acetonitrile, yielded 0.58 g. of 8-chloro-α,α-dimethyldibenzothiophene-3-acetic acid, m.p. 198°–200°.

EXAMPLE 3

Preparation of 8-chloro-α-butyldibenzothiophene-3-acetic acid

To a 500 ml. three-necked flask containing 200 ml. of liquid ammonia and 0.014 mol of sodium amide (prepared from 0.32 g. of sodium) was added dropwise a solution of 3.8 g. of 8-chlorodibenzothiophene-3-acetic acid ethyl ester in 40 ml. of tetrahydrofuran. The solution was stirred for 1 hour and a solution of 1.8 g. of butyl bromide in 50 ml. of ether was added dropwise. The solution was stirred for 1 hour, 0.9 g. of ammonium chloride added and the ammonia allowed to evaporate. The residue was acidified with dilute hydrochloric acid and the oil extracted with ether. The ether was removed by distillation and the residue remaining (3.9 g.) was crude 8-chloro-α-butyldibenzothiophene-3-acetic acid ethyl ester.

To a solution of 0.9 g. of potassium hydroxide in 100 ml. of alcohol was added 3.9 g. of crude 8-chloro-α-butyldibenzothiophene-3-acetic acid ethyl ester. The solution was refluxed for 3 hours and then the solvent was removed in vacuo. Water was added to the residue and the insoluble by-products extracted with ether and the ether discarded. The clear aqueous solution was acidified with dilute hydrochloric acid and the desired product extract with ethyl acetate. The solvent was removed in vacuo and the residue, after crystallization from acetonitrile, yielded 1 g. of 8-chloro-α-butyldibenzothiophene-3-acetic acid, m.p. 156°–159°.

EXAMPLE 4

Preparation of 3-bromo-4-oxocyclohexaneacetic acid ethyl ester 74.0 G. of 4-oxocyclohexaneacetic acid ethyl ester and 1200 ml. of anhydrous ether were placed in a 3 l. three-necked flask, provided with a thermometer, nitrogen inlet, dropping funnel, condenser and stirrer. The solution was cooled to −10° by means of a dry ice-acetone bath, and 64.0 g. of bromine was added dropwise over a period of 30–40 minutes. The resulting colorless solution was washed three times with 100 ml. of water, then two times with 125 ml. of cold saturated sodium bicarbonate solution followed by 100 ml. of water. The combined aqueous solutions were extracted twice with 150 ml. of ether. The combined ether extracts were dried over anhydrous magnesium sulfate, and the ether was removed by distillation from a steam bath at atmospheric pressure to give a residue of crude 3-bromo-4-oxocyclohexaneacetic acid ethyl ester, weighing 105 g.

EXAMPLE 5

Preparation of 3-(4-chlorophenylthio)-4-oxocyclohexaneacetic acid ethyl ester

58 G. of 4-chlorothiophenol and a solution of 26.5 g. of 85% potassium hydroxide in 1500 ml. of ethanol were each placed in a 3 l. three-necked flask, provided with a condenser, nitrogen inlet, dropping funnel and stirrer. The solution was brought to reflux and a solution of 105 g. of crude 3-bromo-4-oxocyclohexaneacetic acid ethyl ester in 500 ml. of ethanol was added over a period of one hour to the refluxing solution. After the addition, the solution was stirred at reflux for one hour, cooled to room temperature, and filtered to remove the potassium bromide. After removal of the ethanol in vacuo (steam bath, rotary evaporator), 300 ml. of water was added to the residue, the product was extracted three times with 200 ml. of ether and the ether extract dried over anhydrous magnesium sulfate. After removal of ether from a steam bath at atmospheric pressure, the residue, weighing 128 g., was distilled in vacuo. A forerun weighing 28.7 g. was collected at 100°-190° (1 mm.), while 76.4 g. of a main fraction collected at 190°-222° (1 mm.). A gas chromatographic determination of the main fraction showed that 3-(4-chlorophenylthio)-4-oxocyclohexaneacetic acid ethyl ester was present.

EXAMPLE 6

Preparation of 8-chloro-1,2,3,4-tetrahydrodibenzothiophene-3-acetic acid ethyl ester 76.4 G. of the above-distilled 3-(4-chlorophenylthio)-4-oxocyclohexaneacetic acid ethyl ester (bp 190–222/1 mm.) was added to 1000 g. of polyphosphoric acid, contained in a 2 l. three-necked flask, provided with a stirrer and condenser. The mixture was heated on a steam bath for 90 minutes and then poured into a mixture of 1 kilogram of ice and 1 liter of water. The mixture was stirred until the dark oily complex was decomposed and a light yellow color appeared. The product was extracted twice with 500 ml. of ether. The ether extract was washed twice with 100 ml. of water, then with 100 ml. of saturated sodium bicarbonate solution, dried over anhydrous potassium carbonate, and distilled at atmospheric pressure from a steam bath to remove the ether to give 57.1 g. of residue. A gas chromatogram of this crude residue showed the presence of 8-chloro-1,2,3,4-tetrahydrodibenzothiophene-3-acetic acid ethyl ester and of bis-(4-chlorophenyl)disulfide.

In order to remove the by-product bis(4-chlorophenyl)disulfide, 30.9 g. of the above crude mixture was added to a 1 liter three-necked flask provided with a condenser and an inlet for nitrogen. A solution of 4.8 g. of sodium hydroxide in 250 ml. of ethanol was added, and the resulting solution was refluxed for 1 hour under nitrogen. The ethanol was removed in vacuo (steam bath, rotary evaporator) and 200 ml. of water added. The solution was acidified with dilute hydrochloric acid. After the precipitated 8-chloro-1,2,3,4-tetrahydrodibenzothiophene acetic acid had settled, the supernatant liquid was decanted. 100 Ml. of ether was added to the wet semi-solid acid, and the mixture swirled. The insoluble 8-chloro-1,2,3,4-tetrahydrodibenzothiopheneacetic acid was filtered off, washed with 50 ml. of ether, and dried in a vacuum oven overnight at 50°. The yield of 8-chloro-1,2,3,4-tetrahydrodibenzothiophene acetic acid was 26 g.), mp 195°-202°. Re-esterification was carried out by adding 25.4 g. of the above acid to 400 ml. of ethanol saturated at room temperature with hydrogen chloride. After the solution was refluxed for 6 hours, the ethanol was removed in vacuo (steam bath, rotary evaporator), and 300 ml. of benzene was added to the residue. The benzene solution was first extracted twice with 75 ml. of water and then twice with 75 ml. of 6% sodium bicarbonate. The benzene solution was dried over anhydrous potassium carbonate and distilled in vacuo to remove the benzene. The weight of the crude ester was 26.6 g., m.p. 55°-60°. Crystallization from hexane gave 22.1 g. of pure 8-chloro-1,2,3,4-tetrahydrodibenzothiophene-3-acetic acid ethyl ester, m.p. 64°-66°.

EXAMPLE 7

Preparation of 8-chloro-dibenzothiophene-3-acetic acid ethyl ester

Into a 2 liter three-necked flask provided with a condenser, stirrer and dropping funnel was added 31.2 g. of 2,3-dichloro-5,6-dicyano-1,4-benzoquinone and 500 ml. of dioxane. To the solution, heated to reflux, was added at a rapid rate a solution of 21.2 g. of 8-chloro-1,2,3,4-tetrahydrodibenzothiophene-3-acetic acid ethyl ester in 500 ml. of dioxane. The solution was refluxed and stirred for 18 hours, cooled to room temperature, and filtered to remove the formed hydroquinone. The solvent was removed in vacuo (steam bath, rotary evaporator), and the residue was dissolved in 300 ml. of methylene chloride. The solution was filtered, if necessary, and passed through a column containing about 200 g. of alumina (Woelm, grade I). The color of the solution was now a light yellow. The solvent was removed (steam bath, rotary evaporator), and the weight of sticky solid was 18.6 g. The latter was recrystallized from hexane and yielded 14 g. of 8-chloro-dibenzothiophene-3-acetic acid ethyl ester, mp 88°-90°.

EXAMPLE 8

Preparation of 8-chloro-dibenzothiophene-3-acetic acid

To a 500 ml. flask, fitted with a condenser and containing a solution of 1.84 g. of sodium hydroxide in 150 ml. of ethanol was added 14 g. of 8-chloro-dibenzothiophene-3-acetic acid ethyl ester. After the solution was refluxed for 1 hour, the solvent was removed in vacuo (steam bath, rotary evaporator), the residue dissolved in 100 ml. of water, and the aqueous solution acidified with dilute hydrochloric acid. The 8-chloro-dibenzothiophene-3-acetic acid was removed by filtration, washed with water and dried at 60° in a vacuum oven overnight. The yield of 8-chloro-dibenzothiophene-3-acetic acid, after crystallization from i-propanol, was 8 g., mp 220°-221°.

EXAMPLE 9

Preparation of 3-(2-chlorophenylthio)-4-ketocyclohexane acetic acid ethyl ester

28 G. of 2-chlorothiophenol and a solution of 10.8 g. of 85% potassium hydroxide in 300 ml. of ethanol were each placed in a 3 liter three-necked flask, provided with a condenser, nitrogen inlet, dropping funnel and stirrer. The solution was brought to reflux and a solution of 50.6 g. of 3-bromo-4-ketocyclohexaneacetic acid ethyl ester in 500 ml. of ethanol was added over a period of one hour to the refluxing solution. After the addition, the solution was stirred at reflux for one hour, cooled to room temperature, and filtered to remove the potassium bromide. After removal of the ethanol in vacuo (steam bath, rotovapor), 300 ml. of water was added to the residue, the product was extracted three times with 200 ml. of ether and the ether extract dried over anhydrous magnesium sulfate. After removal of ether from a steam bath at atmospheric pressure, the residue was distilled in vacuo. A forerun was collected at 100°-190° (1 mm), while a main fraction was collected at 190°-222° (1 mm). The yield of 3-(2-chlorophenylthio)-4-ketocyclohexaneacetic acid ethyl ester from the main fraction was 33.9 g., b.p. 205-215/0.7 mm.

EXAMPLE 10

Preparation of 6-chloro-1,2,3,4-tetrahydrodibenzothiophene-3-acetic acid ethyl ester 33.9 G. of the above distilled 3-(2-chlorophenylthio)-4-ketocyclohexaneacetic acid ethyl ester was added to 600 g. of polyphosphoric acid, contained in a 2 liter, three-necked flask, provided with a stirrer and condenser. The mixture was heated on a steam bath for 90 minutes and then poured into a mixture of 1 kilogram of ice and 1 liter of water. The mixture was stirred until the dark oily complex was decomposed and a light yellow color appeared. The product was extracted twice with 500 ml. of ether. The ether extract was washed twice with 100 ml. of water, then with 100 ml. of saturated sodium bicarbonate solution, dried over anhydrous potassium carbonate, and distilled at atmospheric pressure from a steam bath to remove the ether. The yield of 6-chloro-1,2,3,4-tetrahydrodibenzothiophene-3-acetic acid ethyl ester was 8.5 g., b.p. 195–210/0.7 mm, mp 51°–53° (pentane).

EXAMPLE 11

Preparation of 6-chloro-dibenzothiophene-3-acetic acid ethyl ester

Into a 2 liter three-necked flask provided with a condenser, stirrer and dropping funnel was added 6 g. of 2,3-dichloro-5,6-dicyano-1,4-benzoquinone and 500 ml. of dioxane. To the solution, heated to reflux, was added at a rapid rate a solution of 3.3 g. of 6-chloro-1,2,3,4-tetrahydrodibenzothiophene-3-acetic acid ethyl ester in 50.0 ml. of dioxane. The solution was refluxed and stirred for 18 hours, cooled to room temperature, and filtered to remove the hydroquinone. The solvent was removed in vacuo (steam bath, rotary evaporator) and the residue was dissolved in 300 ml. of methylene chloride. The solution was filtered, if necessary, and passed through a column containing about 200 g. of alumina (Woelm, grade I). The solvent was removed (steam bath, rotary evaporator). The resulting solid was recrystallized from hexane and yielded 1.3 g. of 6-chlorodibenzothiophene-3-acetic acid ethyl ester, mp 62°–64° (hexane).

EXAMPLE 12

Preparation of 6-chloro-dibenzothiophene-3-acetic acid

To a 100 ml. flask, fitted with a condenser and containing a solution of 0.24 g. of potassium hydroxide in 30 ml. of ethanol was added 1.3 g. of 6-chlorodibenzothiophene-3-acetic acid ethyl ester. After the solution was refluxed for 1 hour, the solvent was removed in vacuo (steam bath, rotary evaporator), the residue dissolved in 100 ml. of water, and the aqueous solution acidified with dilute hydrochloric acid. The 6-chlorodibenzothiophene-3-acetic acid was removed by filtration, washed with water and dried at 60° in a vacuum oven overnight. The yield of 6-chlorodibenzothiophene-3-acetic acid, after crystallization from acetonitrile was 0.8 g., mp 226°–228°.

EXAMPLE 13

Preparation of 3-(4-i-butylphenylthio)-4-ketocyclohexaneacetic acid ethyl ester 31.4 G. of 4-i-butylthiophenol and a solution of 10.6 g. of 85% potassium hydroxide in 300 ml. of ethanol were each placed in a 3 liter three-necked flask, provided with a condenser, nitrogen inlet, dropping funnel and stirrer. The solution was brought to reflux and a solution of 49.5 g. of 3-bromo-4-ketocyclohexaneacetic acid ethyl ester in 500 ml. of ethanol was added over a period of one hour to the refluxing solution. After the addition, the solution was stirred at reflux for one hour, cooled to room temperature, and filtered to remove the potassium bromide. After removal of the ethanol in vacuo (steam bath, rotary evaporator), 300 ml. of water was added to the residue, the product was extracted three times with 200 ml. of ether and the ether extract dried over anhydrous magnesium sulfate. After removal of ether from a steam bath at atmospheric pressure, the residue was distilled in vacuo. A yield of 42.5 g. of 3-(4-i-butylphenylthio)-4-ketocyclohexane acetic acid ethyl ester was obtained, b.p. 205–220/2.0 mm.

EXAMPLE 14

Preparation of 8-i-butyl-1,2,3,4-tetrahydrodibenzothiophene-3-acetic acid ethyl ester 42.5 G. of the above distilled 3-(4-i-butylphenylthio)-4-ketocyclohexane acetic acid ethyl ester was added to 700 g. of polyphosphoric acid, contained in a 2 liter three-necked flask, provided with a stirrer and condenser. The mixture was heated on a steam bath for 90 minutes and then poured into a mixture of 1 kilogram of ice and 1 liter of water. The mixture was stirred until the dark oily complex was decomposed and a light yellow color appeared. The product was extracted twice with 500 ml. of ether. The ether extract was washed twice with 100 ml. of water, then with 100 ml. of saturated sodium bicarbonate solution, dried over anhydrous potassium carbonate, and distilled at atmospheric pressure from a steam bath to remove the ether. The yield of 8-i-butyl-1,2,3,4-tetrahydrodibenzothiophene-3-acetic acid ethyl ester was 24.4 g., b.p. 195–205/0.7 mm.

EXAMPLE 15

Preparation of 8-i-butyldibenzothiophene-3-acetic acid ethyl ester

Into a 2 liter three-necked flask provided with a condenser, stirrer and dropping funnel was added 16.6 g. of 2,3-dichloro-5,6-dicyano-1,4-benzoquinone and 200 ml. of xylene. To the solution, heated to reflux, was added at a rapid rate a solution of 10.7 g. of 8-i-butyl-1,2,3,4-tetrahydrodibenzothiophene-3-acetic acid ethyl ester in 200 ml. of xylene. The solution was refluxed and stirred for 18 hours, cooled to room temperature, and filtered to remove the hydroquinone. The solvent was removed in vacuo (steam bath, rotary evaporator) and the residue was dissolved in 300 ml. of methylene chloride. The solution was filtered, if necessary, and passed through a column containing about 200 g. of alumina (Woelm, grade I). The solvent was removed (steam bath, rotary evaporator). The product was recrystallized from hexane and yielded 4.7 g. of 8-i-butyldibenzothiophene-3-acetic acid ethyl ester, b.p. 200–215/0.7 mm.

EXAMPLE 16

Preparation of 8-i-butyl-dibenzothiophene-3-acetic acid

To a 500 ml. flask, fitted with a condenser and containing a solution of 0.81 g. of potassium hydroxide in 125 ml. of ethanol was added 4.7 g. of 8-i-butyldibenzothiophene-3-acetic acid ethyl ester. After the solution was refluxed for 1 hour, the solvent was removed in vacuo (steam bath, rotary evaporator), the residue dissolved in 100 ml. of water, and the aqueous solution acidified with dilute hydrochloric acid. The product was removed by filtration, washed with water and dried at 60° in a vacuum oven overnight. The yield of 8-i-butyl-dibenzothiophene-3-acetic acid after crystallization from i-propanol was 1.5 g., mp 133°–135° (heptane).

EXAMPLE 17

Preparation of 9-chlorodibenzothiophene-3-acetic acid (A) 3-(3-chlorophenylthio)-4-oxocyclohexaneacetic acid ethyl ester In a 3-l. three-necked flask, provided with a condenser, nitrogen inlet, dropping funnel and stirrer were placed 23.8 g. of 3-chlorothiophenol and a solution of 10.8 g. of 85% potassium hydroxide in 300 ml. of ethanol. The solution was brought to reflux, and a solution of 43 g. of 3-bromo-4-oxocyclohexaneacetic acid ethyl ester in 250 ml. of ethanol was added over a period of one hour. After the addition, the solution was stirred at reflux for one hour, cooled to room temperature and filtered to remove the potassium bromide. After removal of the ethanol in vacuo on the steam bath, 150 ml. of water was added to the residue, the product extracted three times with 100 ml. of ether, and the ether extract was dried over anhydrous magnesium sulfate. After removal of the ether from a steam bath at atmospheric pressure, the residue was distilled in vacuo. The yield of 3-(3-chlorophenylthio)-4-oxocyclohexaneacetic acid ethyl ester was 12.2 g.; b.p. 195°–225°/2 mm.

(B) 9-chloro-1,2,3,4-tetrahydrodibenzothiophene-3-acetic acid ethyl ester

To 200 g. of polyphosphoric acid contained in a 1-l. three-necked flask, provided with a stirrer and condenser was added 8.0 g. of 3-(3-chlorophenylthio)-4-oxocyclohexaneacetic acid ethyl ester. The mixture was heated on a steam bath for 90 minutes and then poured into a mixture of 200 g. of ice and 200 ml. of water with stirring, which was continued until the dark oily complex was decomposed and a light yellow color appeared. The product was extracted twice with 200 ml. of ether. The ether extract was washed twice with 50 ml. of water and then with 50 ml. of saturated sodium bicarbonate solution. The solution was dried over anhydrous potassium carbonate and then filtered. The ether was removed on a steam bath in a rotary evaporator at atmospheric pressure, and the residue was distilled at reduced pressure. At 205°–220°/2 mm. a yield of 3.3 g. of 9-chloro-1,2,3,4-tetrahydrodibenzothiophene-3-acetic acid ethyl ester was obtained.

(C) 9-chlorodibenzothiophene-3-acetic acid ethyl ester

To a 1-l. three-necked flask provided with a condenser, stirrer and dropping funnel was added 11 g. of 2,3-dichloro-5,6-dicyano-1,4-benzoquinone (DDQ) and 500 ml. of dioxane. To the solution heated to reflux, was added at a rapid rate a solution of 6 g. of 9-chloro-1,2,3,4-tetrahydrodibenzothiophene-3-acetic acid ethyl ester in 100 ml. of dioxane. The solution was refluxed and stirred for 24 hours, cooled to room temperature and then filtered to remove the hydroquinone. The solvent was removed in vacuo on the steam bath, and the residue was dissolved in 200 ml. of methylene chloride. This solution was passed through a column containing about 150 g. of alumina (Woelm, grade 1). The solvent was removed on the steam bath and the residue was crystallized from alcohol. The yield of 9-chlorodibenzothiophene-3-acetic acid ethyl ester was 1.1 g., m.p. 82°–84°.

(D) 9-chlorodibenzothiophene-3-acetic acid

To a 100 ml. flask, fitted with a condenser and containing a solution of 0.28 g. of potassium hydroxide in 50 ml. of ethanol was added 1.1 g. of 9-chlorodibenzothiophene-3-acetic acid ethyl ester. After the solution was refluxed for four hours, the solvent was removed in vacuo on the steam bath, the residue was dissolved in 50 ml. of water, and the aqueous solution was acidified with dilute hydrochloric acid. The product was filtered, washed with 20 ml. of water, and dried at 60° in a vacuum oven for 12 hours. The yield of 9-chlorodibenzothiophene-3-acetic acid, after crystallization from methanol, was 0.8 g. (m.p. 203°–206°).

EXAMPLE 18

Preparation of 8-methyldibenzothiophene-3-acetic acid (A) 3-(4-methylphenylthio)-4-ketocyclohexanecarboxylic acid ethyl ester In a 2 l. three-necked flask provided with a condenser, nitrogen inlet, dropping funnel and stirrer were placed 73.5 g. of p-toluenethiol and a solution of 33 g. of 85% potassium hydroxide in 500 ml. of ethanol. The solution was brought to reflux, and a solution of 146.4 g. of 3-bromo-4-ketocyclohexanecarboxylic acid ethyl ester in 500 ml. of ethanol was added over a period of one hour. After the addition, the solution was stirred at reflux for one hour. After removal of the ethanol in vacuo on the steam bath, 300 ml. of water was added, and the product was extracted three times with 200 ml. of ether. The ether solution was dried over anhydrous magnesium sulfate, and then the solvent was removed on the steam bath. The residue was crystallized from heptane; yield 66 g. of 3-(4-methylphenylthio)-4-ketocyclohexanecarboxylic acid ethyl ester, m.p. 87°–89°.

(B) 8-methyl-1,2,3,4-tetrahydrodibenzothiophene-3-carboxylic acid ethyl ester

To 130 g. of polyphosphoric acid contained in a 500 ml. three-necked flask provided with a stirrer and condenser, was added 13 g. of 3-(4-methylphenylthio)-4-ketocyclohexanecarboxylic acid ethyl ester. The mixture was heated on a steam bath for 90 minutes and then poured onto a mixture of 200 g. of ice and 200 ml. of water. The mixture was stirred until the dark oily complex was decomposed, and a light yellow color appeared. The product was extracted with ether, and the solution then washed with water until it was neutral. After drying over anhydrous potassium carbonate, the ether was distilled off on the steam bath, and the residue was crystallized from methanol. The yield of 8-methyl-1,2,3,4-tetrahydrodibenzothiophene-3-carboxylic acid ethyl ester, m.p. 68°–69°, was 6 g.

(C) 8-methyldibenzothiophene-3-carboxylic acid ethyl ester

To a 500 ml. three-necked flask provided with a condenser, stirrer and dropping funnel was added 10 g. of 2,3-dichloro-5,6-dicyano-1,4-benzoquinone (DDQ) and 200 ml. of dioxane. To the solution, heated to reflux, was added at a rapid rate a solution of 5.5 g. of 8-methyl-1,2,3,4-tetrahydrodibenzothiophene-3-carboxylic acid ethyl ester in 50 ml. of dioxane. The solution was refluxed and stirred for 20 hours, cooled to room temperature and filtered to remove the hydroquinone. The solvent was removed in vacuo on the steam bath, and the residue was dissolved in 100 ml. of methylene chloride. The solution was passed through a column containing about 75 g. of alumina (Woelm, grade I). The solvent was removed, and the residue was crystallized from methanol. The yield of 8-methyldibenzothiophene-3-carboxylic acid ethyl ester was 4.2 g., m.p. 83°–87°.

(D) 8-methyldibenzothiophene-3-carboxylic acid

To a solution of 0.73 g. of potassium hydroxide in 50 ml. of ethanol was added 3.5 g. of 8-methyldibenzothiophene-3-carboxylic acid ethyl ester. The solution was refluxed for 3 hours. The solvent was removed in vacuo on the steam bath, and the crude potassium salt was dissolved in 50 ml. of water. The solution was acidified with dilute hydrochloric acid and the product was filtered off and dried. The yield of 8-methyldibenzothiophene-3-carboxylic acid was 2 g., m.p. 290°–291°.

(E) 3-chlorocarbonyl-8-methyldibenzothiophene

A solution of 3 g. of oxalyl chloride in 50 ml. of benzene was added dropwise with stirring to a suspension of 3.5 g. of the crude potassium salt of 8-methyldibenzothiophene-3-carboxylic acid in 100 ml. of benzene. The mixture was filtered and the solvent removed in vacuo on the steam bath. The residue, after crystallization from hexane, yielded 2.5 g. of 3-chlorocarbonyl-8-methyldibenzothiophene, m.p. 127°–128°.

(F) 3-diazomethylcarbonyl-8-methyldibenzothiophene

A solution of 2.5 g. of 3-chlorocarbonyl-8-methyldibenzothiophene in 75 ml. of ether was added dropwise to a solution of 0.81 g. of diazomethane in 100 ml. of ether in an ice bath. The solution was stirred overnight, and the ether was removed on the steam bath. The crude product (2.5 g.), 3-diazomethylcarbonyl-8-methyldibenzothiophene, was used directly in the next step.

(G) 8-methyldibenzothiophene-3-acetic acid ethyl ester

To a refluxing solution of 2.5 g. of crude 3-diazomethylcarbonyl-8-methyldibenzothiophene in 50 ml. of alcohol was added dropwise, with stirring, a solution of 1.0 g. of silver benzoate in 10 ml. of triethylamine. The solution was refluxed until evolution of nitrogen had ceased. The solution was filtered, and the solvent was removed in vacuo on the steam bath. The residue was crystallized from petroleum ether (30°–60°) to yield 1.3 g. of 8-methyldibenzothiophene-3-acetic acid ethyl ester, m.p. 45°–48°.

(H) 8-methyldibenzothiophene-3-acetic acid

To a solution of 0.27 g. of potassium hydroxide in 50 ml. of alcohol, was added 1.3 g. of 8-methyldibenzothiophene-3-acetic acid ethyl ester, and the solution was refluxed for 3 hours. The solvent was removed in vacuo, and the residue was dissolved in 50 ml. of water. The solution was acidified with dilute hydrochloric acid and the product was filtered off and dried. Recrystallization from acetonitrile yielded 0.5 g. of 8-methyldibenzothiophene-3-acetic acid, m.p. 185°–187°.

EXAMPLE 19

Preparation of dibenzothiophene-3-acetic acid (A) 3-bromo-4-ketocyclohexanecarboxylic acid ethyl ester To a 1 l. three-necked flask provided with a stirrer, condenser and dropping funnel and containing a solution of 25.5 g. of 4-ketocyclohexanecarboxylic acid ethyl ester in 450 ml. of anhydrous ether cooled to −10° was added dropwise over 45 minutes 24 g. of bromine. The resulting colorless solution was washed with 3×100 ml. of water, then with 2×50 ml. of 5% sodium bicarbonate solution and finally with 2×100 ml. of water. The ether solution was dried over anhydrous magnesium sulfate and then the solvent was removed on a steam bath. The yield of crude 3-bromo-4-ketocyclohexanecarboxylic acid ethyl ester was 37 g.

(B) 3-phenylthio-4-ketocyclohexanecarboxylic acid ethyl ester

In a 2 l. three-necked flask provided with a condenser, nitrogen inlet, dropping funnel and stirrer, were placed 16.5 g. of benzenethiol and a solution of 10 g. of potassium hydroxide in 400 ml. of alcohol. The solution was brought to reflux and a solution of 37 g. of 3-bromo-4-ketocyclohexanecarboxylic acid ethyl ester in 200 ml. of alcohol was added over a period of 1 hour. The reaction mixture was then stirred and refluxed for 1 hour. The solvent was removed on a steam bath at reduced pressure and 200 ml. of water added to the residue. The oil was extracted with ether and the solution dried over anhydrous potassium carbonate. The ether was removed on a steam bath and the residue, on vacuum distillation, yielded 20 g. of 3-phenylthio-4-ketocyclohexanecarboxylic acid ethyl ester, b.p. 198°–210° at 2 mm.

(C) 1,2,3,4-tetrahydrodibenzothiophene-3-carboxylic acid ethyl ester

A mixture of 10 g. of 3-phenylthio-4-ketocyclohexane carboxylic acid ethyl ester and 130 g. of polyphosphoric acid was stirred on a steam bath for 1.5 hours. It was then poured onto a mixture of 400 g. of ice and 400 ml. of water. The oil was extracted with 2×100 ml. of ether and the ether extract washed with 2×50 ml. of water and then with 50 ml. of 5% sodium bicarbonate solution. The ether solution was dried over anhydrous potassium carbonate, and the solvent then removed on a steam bath. The crude product was distilled at reduced pressure and yielded 5 g. of 1,2,3,4-tetrahydrodibenzothiophene-3-carboxylic acid ethyl ester, b.p. 190°–195° at 2 mm.

(D) Dibenzothiophene-3-carboxylic acid ethyl ester

To a solution of 2.5 g. of 1,2,3,4-tetrahydrodibenzothiophene-3-carboxylic acid ethyl ester in 100 ml. of dioxane was added 4.7 g. of 2,3-dichloro-5,6dicyano-1,4-benzoquinone. The solution was stirred and refluxed for 31 hours. The solution was cooled and the hydroquinone filtered off. The dioxane was removed on a steam bath under reduced pressure. The residue was dissolved in 100 ml. of methylene chloride and the solution passed through a column containing about 75 g. of alumina (Woelm, grade 1). The solvent was removed on a steam bath and the residue crystallized from hexane. The yield of dibenzothiophene-3-carboxylic acid ethyl ester, m.p. 74°–78° was 1.7 g.

(E) Dibenzothiophene-3-carboxylic acid potassium salt

To 200 ml. of alcohol containing 2.7 g. of potassium hydroxide was added 13.2 g. of dibenzothiophene-3-carboxylic acid ethyl ester and the solution was refluxed, stirred for 4 hours and filtered. The insoluble dibenzothiophene-3-carboxylic acid potassium salt was filtered off and weighed, after drying at 80° in a vacuum oven, 8.9 g. The dibenzothiophene-3-carboxylic acid, which can be obtained from the above potassium salt is a known compound [H. Gilman, A. L. Jacoby and H. A. Pacevitz, J. Org. Chem. 3, 120 (1938)].

(F) 3-chlorocarbonyldibenzothiophene

To a suspension of 8.9 g. of dibenzothiophene-3-carboxylic acid potassium salt in 200 ml. of benzene was added dropwise with stirring over a period of 30 minutes, a solution of 6.4 g. of oxalyl chloride in 50 ml. of benzene. The mixture was stirred and refluxed for two hours. The mixture was filtered and the solvent was removed in vacuo on the steam bath. The residue, 3-chlorocarbonyldibenzothiphene (7.9 g.) was used directly in the next step.

(G) 3-diazomethylcarbonyldibenzothiophene

A solution of 7.9 g. of crude 3-chlorocarbonyldibenzothiophene in 700 ml. of ether was added with stirring to a solution of 2.7 g. of diazomethane in 180 ml. of ether in an ice bath. The solution was stirred for 7 hours and then the solvent was removed, on a steam bath, to yield the crude 3-diazomethylcarbonyldibenzothiophene (7.5 g.) which was used directly in the next step.

(H) Dibenzothiophene-3acetic acid ethyl ester

To a refluxing solution of 7.5 g. of crude 3-diazomethylcarbonyldibenzothiophene in 100 ml. of alcohol was added, dropwise with stirring, a solution of 1 g. of silver benzoate in 10 ml. of triethylamine. The solution was then refluxed for one hour, filtered, and the solvent was removed in vacuo. The residue, after crystallization from petroleum ether (30°-60°) yielded 2.7 g. of dibenzothiophene-3-acetic acid ethyl ester, m.p. 60°-62°.

(I) Dibenzothiophene-3-acetic acid

To a solution of 0.56 g. of potassium hydroxide in 75 ml. of ethanol was added 2.7 g. of dibenzothiophene-3-acetic acid ethyl ester. The solution was refluxed 3 hours and the solvent then removed in vacuo. The residue was dissolved in 50 ml. of water, and the solution was acidified with dilute hydrochloric acid. The solid was filtered off and dried in vacuo at 50°. Recrystallization from acetonitrile yielded 1 g. of dibenzothiophene-3-acetic acid, m.p. 174°-176°.

EXAMPLE 20

Preparation of 7-chlorobidenzothiophene-3-acetic acid (A) Dibenzothiophene-3-carboxylic acid ethyl ester 5-oxide 8.3 G. of chlorine was bubbled into a solution of 23.8 g. of dibenzothiophene-3-carboxylic acid ethyl ester in 600 ml. of carbon tetrachloride cooled to 5°. The solution was poured onto ice, and the mixture was well shaken. The solid was filtered off, dried in vacuum at 50° and then crystallized from acetonitrile to yield 11.6 g. of dibenzothiophene-3-carboxylic acid ethyl ester 5-oxide, m.p. 210°-213°.

(B) 7-nitrodibenzothiophene-3-carboxylic acid ethyl ester 5-oxide

To 250 ml. of 90% nitric acid kept at 22°-25°, 25 g. of dibenzothiophene-3-carboxylic acid ethyl ester 5-oxide was added, in portions. The solution was stirred for 15 minutes and then poured onto ice. The solid was filtered off, washed with water until neutral and dried in a vacuum oven at 50°. The solid was crystallized from 1,2-dichloroethane to yield 24.7 g. of 7-nitrodibenzothiophene-3-carboxylic acid ethyl ester 5-oxide, m.p. 245°-250°.

(C) 7-aminodibenzothiophene-3-carboxylic acid ethyl ester hydrochloride

A mixture of 21.9 g. of 7-nitrodibenzothiophene-3-carboxylic acid ethyl ester 5-oxide, 250 ml. of acetic acid, and 1.7 g. of 10% palladium on carbon was shaken at an initial pressure of 50 pounds of hydrogen and heated to 60°. After one hour the uptake of hydrogen had ceased. The mixture was removed from the hydrogenation apparatus, cooled to room temperature and filtered. After removal of the solvent in vacuo on the steam bath, the residue was dissolved in 300 ml. of ethyl acetate, and the product was precipitated as the hydrochloride by bubbling in hydrogen chloride. The yield of 7-aminodibenzothiophene-3-carboxylic acid ethyl ester hydrochloride was 17.1 g. (m.p. 260°-265°). A small portion, after crystallization from methanol, melted at 270°-275°.

(D) 7-chlorodibenzothiophene-3-carboxylic acid ethyl ester

A solution of 28.7 g. of 7-aminodibenzothiophene-3-carboxylic acid ethyl ester hydrochloride in 300 ml. of acetic acid was added at 15° to nitrosylsulfuric acid prepared from 19.4 g. of sodium nitrite and 100 ml. of concentrated sulfuric acid. The mixture was stirred for 15 minutes and then 1 l. of ether was added to precipitate the diazonium sulfate. The mixture of the diazonium sulfate and sodium sulfate was filtered off, washed with ether, and air-dried. The mixture was then added, in portions at 5° to a cuprous chloride solution prepared from 9.4 g. of cuprous chloride, 375 ml. of water and 280 ml. of conc. hydrochloric acid. After the addition, the contents were heated on a steam bath until nitrogen evolution ceased. The solid was filtered off, washed with water and then dried in a vacuum oven. The solid, after crystallization from hexane, yielded 18 g. of 7-chlorodibenzothiophene-3-carboxylic acid ethyl ester, m.p. 120°-122°.

(E) 7-chlorodibenzothiophene-3-carboxylic acid potassium salt

A solution of 4.1 g. of potassium hydroxide (85%) in 100 ml. of alcohol was added to a solution of 18.1 g. of 7-chlorodibenzothiophene-3-carboxylic acid ethyl ester in 450 ml. of warm ethanol. The combined solutions were stirred and refluxed for 8 hours. After cooling to room temperature, the mixture was filtered to give 16.5 g. of the potassium salt.

(F) 3-chlorocarbonyl-7-chlorodibenzothiophene

A solution of 10.5 g. of oxalyl chloride in 100 ml. of benzene was added, with stirring, to a suspension of 16.53 g. of 7-chlorodibenzothiophene-3-carboxylic acid potassium salt in 100 ml. of benzene. The mixture was stirred and refluxed for two hours and then filtered. On distillation to dryness on the steam bath in vacuo 9 g. of crude 3-chlorocarbonyl-7-chlorodibenzothiophene was obtained as a residue.

(G) 7-chlorodibenzothiophene-3-acetic acid ethyl ester

A solution of 9 g. of 3-chlorocarbonyl-7-chlorodibenzothiophene in 100 ml. of dioxane was added dropwise to a solution of 5.3 g. of diazomethane in 250 ml. of ether with cooling in an ice bath. The solution was stirred overnight, and the solvent was then removed by distillation in vacuo. The residue was dissolved in 600 ml. of alcohol, and to the refluxing solution was added dropwise over one hour a solution of 1 g. of silver benzoate in 100 ml. of triethylamine. The solution was refluxed for one hour after the addition and then filtered. The solvent was removed by distillation in vacuo from a steam bath and the residue was crystallized from hexane, yield, 4.8 g. of 7-chlorodibenzothiophene-3-acetic acid ethyl ester, m.p. 68°–70°.

(H) 7-chlorodibenzothiophene-3-acetic acid

To a solution of 1 g. of potassium hydroxide in 75 ml. of alcohol was added 4.8 g. of 7-chlorodibenzothiophene-3-acetic acid ethyl ester. After refluxing for 3 hours, the solvent was removed in vacuo on the steam bath, and 50 ml. of water was added to dissolve the residue. The aqueous solution was acidified with hydrochloric acid, and the product filtered off. The solid was crystallized from acetonitrile to yield 1.7 g. of 7-chlorodibenzothiophene-3-acetic acid, m.p. 198°–200°.

EXAMPLE 21

Preparation of 7-dimethylaminodibenzothiophene-3-acetic acid ethyl ester (A) 7-aminodibenzothiophene-3-carboxylic acid ethyl ester hydrochloride A mixture of 24 g. of 7-nitrodibenzothiophene-3-carboxylic acid ethyl ester 5-oxide, 200 ml. of acetic acid and 2.4 g. of 10% palladium carbon was hydrogenated at 50° at an initial pressure of 50 lbs. After completion of the hydrogenation in 3 hours, the mixture was filtered, and the acetic acid was removed in vacuo (steam bath, rotary evaporator). The residue was dissolved in 250 ml. of ethyl acetate, and hydrogen chloride was bubbled into the solution. The precipitated hydrochloride of 7-aminodibenzothiophene-3-carboxylic acid ethyl ester weighed 20 g.; mp 270°–275°.

(B) 7-dimethylaminodibenzothiophene-3-carboxylic acid ethyl ester

A mixture of 7.3 g. of 7-aminodibenzothiophene-3-carboxylic acid ethyl ester hydrochloride and 5.0 g. of trimethyl phosphate were heated at 160° for 45 minutes. After cooling to room temperature, 75 ml. of ethyl acetate was added, and the solution was extracted with 25 ml. of water. The ethyl acetate was removed in vacuo (steam bath, rotary evaporator), and the residue was crystallized from ethanol. The yield of 7-dimethylaminodibenzothiophene-3-carboxylic acid ethyl ester was 2.8 g.; mp 160°–162°.

(C) 7-dimethylaminodibenzothiophene-3carboxylic acid potassium salt

To a solution of 0.5 g. of potassium hydroxide in 100 ml. of ethanol was added 2.8 g. of 7-dimethylaminodibenzothiophene-3-carboxylic acid ethyl ester. The solution was stirred and refluxed for 3 hours during which time the potassium salt precipitated. The salt was filtered off, washed with ether and air dried. The yield of 7-dimethylaminodibenzothiophene-3-carboxylic acid potassium salt was 1.9 g.

(D) 7-dimethylaminodibenzothiophene-3-carbonyl chloride

To a suspension of 1.9 g. of 7-dimethylaminodibenzothiophene-3-carboxylic acid potassium salt in 100 ml. of refluxing benzene was added over a period of 20 minutes a solution of 1.2 g. of oxalyl chloride in 25 ml. of benzene. The solution was then stirred and refluxed for 3 hours. The hot solution was filtered, and the filtrate was distilled to dryness in vacuo (steam bath, rotary evaporator). The residue of crude 7-dimethylaminodibenzothiophene-3-carbonyl chloride weighed 1.8 g.

(E) 7-dimethylaminodibenzothiophene-3-acetic acid ethyl ester

To a 250 ml. 3-necked flask provided with a stirrer, dropping funnel and condenser was added a solution of 0.7 g. of diazomethane in 50 ml. of ether. The flask was cooled in an ice bath, and a solution of 1.8 g. of 7-dimethylaminodibenzothiophene-3-carbonyl chloride in 50 ml. of anhydrous ether and 50 ml. of tetrahydrofuran was added dropwise over a period of 15 minutes. The ice bath was removed and the solution stirred for 2.5 hours. After removal of the solvent by distillation in vacuo on the steam bath, the residue was crystallized from toluene. The yield of 3-diazomethylcarbonyl-7-dimethylaminodibenzothiophene was 0.3 g; mp 173°–175°. To a refluxing solution of the diazo compound (0.3 g.) in 50 ml. of alcohol was added dropwise, over 1 hour with stirring, a solution of 1 g. of silver benzoate in 10 ml. of triethylamine. The solution was filtered and the solvents removed from a steam bath in vacuo. The residue was crystallized from methanol and yielded 50 mg. of 7-dimethylaminodibenzothiophene-3-acetic acid ethyl ester; mp 115°–120°.

EXAMPLE 22

Preparation of 8-chlorodibenzothiophene-3-acetamide

A solution of 2.76 g. of 8-chlorodibenzothiophene-3-acetic acid in 10 ml. of thionyl chloride was stirred for 1 hour and then distilled at reduced pressure at room temperature. The residue of crude 8-chlorodibenzothiophene-3acetyl chloride, m.p. 92°–99°, was then dissolved in 100 ml. of benzene, and the solution was saturated with ammonia. The amide was filtered off, washed with water and crystallized from acetic acid. The product, 8-chlorodibenzothiophene-3acetamide weighed 2 g. and melted at 237°–238°.

EXAMPLE 23

Preparation of 8-chlorodibenzothiophene-3-ethanol 3.05 G. of 8-chlorodibenzothiophene-3-acetic acid ethyl ester was added to 0.45 g. of lithium aluminum hydride in 100 ml. of ether. The solution was refluxed for one hour and then treated with 2 ml. of water. The solution was filtered and the ether removed from a steam bath. The residue was crystallized from acetonitrile and yielded 1.1 g. of 8-chlorodibenzothiophene-3-ethanol, m.p. 98°–100°.

EXAMPLE 24

Preparation of 8-chlorodibenzothiophene-3-acetic acid, 2-dimethylaminoethyl ester hydrochloride A mixture of 2.76 g. of 8-chlorodibenzothiophene-3-acetic acid, 3.04 g. of potassium carbonate, 1.73 g. of dimethylaminoethyl chloride hydrochloride, and 250 ml. of dimethylformamide was stirred and heated at 120° for 4 hours. The solvent was removed in vacuo on the steam bath, and 75 ml. of water added to the residue. The oil was extracted with ethyl acetate and the crude product precipitated as the hydrochloride by the addition of hydrogen chloride. On crystallization from acetone, 1.5 g. of 8-chlorodibenzothiophene-3-acetic acid 2-dimethylaminoethyl ester hydrochloride, m.p. 179°–181°, was obtained.

EXAMPLE 25

| Tablet Formulation | |
| --- | --- |
| | Per Tablet |
| Racemic 8-chloro-dibenzothiophene-3-acetic acid | 25 mg. |
| Dicalcium Phosphate Dihydrate, unmilled | 175 mg. |
| Corn Starch | 24 mg. |
| Magnesium Stearate | 1 mg. |
| Total Weight | 225 mg. |

Procedure:

1. 25 Parts of racemic 8-chloro-dibenzothiophene-3-acetic acid and 24 parts of corn starch are mixed together and passed through a No. 00 screen in Model "J" Fitzmill with hammers forward.

2. This premix is then mixed with 175 parts of dicalcium phosphate and onehalf of a part of the magnesium stearate, and passed through a No. 1A screen in Model "J" Fitzmill with knives forward, and slugged.

3. The slugs are passed through a No. 2A plate in a Model "D" Fitzmill at slow speed with knives forward, and the other one-half of a part magnesium stearate is added.

4. The mixture is mixed and compressed into tablets weighing 225 mg.

EXAMPLE 26

| Capsule Formulation | |
| --- | --- |
| | Per Capsule |
| Racemic 8-chloro-dibenzothiophene-3-acetic acid | 50 mg. |
| Lactose, U.S.P. | 125 mg. |
| Corn Starch, U.S.P. | 30 mg. |
| Talc, U.S.P. | 5 mg. |
| Total Weight | 210 mg. |

Procedure:

1. 50 Parts of racemic 8-chloro-dibenzothiophene-3-acetic acid is mixed with 125 parts of lactose and 30 parts of corn starch in a suitable mixer.

2. The mixture is further blended by passing through a Fitzpatrick Comminuting Machine with a No. 1A screen with knives forward.

3. The blended powder is returned to the mixer, 5 parts talc are added and blended thoroughly.

4. The mixture is filled into No. 4 hard shell gelatin capsules on a Parke Davis capsulating machine.

EXAMPLE 27

| Tablet Formulation | |
| --- | --- |
| | Per Tablet |
| Racemic 8-chloro-dibenzothiophene-3-acetic acid | 100 mg. |
| Lactose, U.S.P. | 202 mg. |
| Corn Starch, U.S.P. | 80 mg. |
| Amijel BOLL[1] | 20 mg. |
| Calcium Stearate | 8 mg. |
| Total Weight | 410 mg. |

[1]A prehydrolyzed food grade corn starch. Any similar prehydrolyzed corn starch may be used.

[1]A prehydrolyzed food grade corn starch. Any similar prehydrolyzed corn starch may be used.

Procedure:

1. 100 Parts of racemic 8-chloro-dibenzothiophene-3-acetic acid, 202 parts of lactose, 80 parts of corn starch and 20 parts Amijel BO11 are blended in a suitable mixer.

2. The mixture is granulated to a heavy paste with water and the moist mass is passed through a No. 12 screen. It is then dried overnight at 110° F.

3. The dried granules are passed through a No. 16 screen and transferred to a suitable mixer. The calcium stearate is added and mixed until uniform.

4. The mixture is compressed at a tablet weight of 410 mg. using tablet punches having a diameter of approximately 154". (Tablets may be either flat or biconvex and may be scored if desired.)

EXAMPLE 28

| Suppository Formulation | |
| --- | --- |
| | Per 1.3 Gm. Suppository |
| Racemic 8-chloro-dibenzothiophene-3-acetic acid | 0.025 mg. |
| Hydrogenated coconut oil | 1.230 mg. |
| Carnauba Wax | 0.045 gm. |

Procedure:

1. 123 parts of hydrogenated coconut oil and 4.5 parts of carnauba wax are melted in a suitable size glass-lined container (stainless steel may also be used), mixed well and cooled to 45° C.

2. 2.5 Parts of racemic 8-chloro-dibenzothiophene-3-acetic acid, which has been reduced to a fine powder with no lumps, is added and stirred until completely and uniformly dispersed.

3. The mixture is poured into suppository molds to yield suppositories having an individual weight of 1.3 gms.

4. The suppositories are cooled and removed from molds, and individually wrapped in wax paper for packaging. (Foil may also be used.)

We claim:

1. A compound of the formula

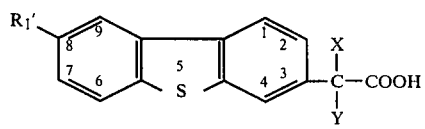

wherein R'₁ is halogen, and X and Y, independently, are hydrogen or lower alkyl, or when X and Y are different, its enantiomers.

2. A compound in accordance with claim 1, racemic 8-chloro-α-methyldibenzothiophene-3acetic acid.

3. A compound in accordance with claim 2, (+) 8-chloro-α-methyldibenzothiophene-3-acetic acid.

4. A compound in accordance with claim 2, (−) 8-chloro-α-methyldibenzothiophene-3-acetic acid.

5. A compound in accordance with claim 1, 8-chloro-dibenzothiophene-3-acetic acid.

* * * * *